United States Patent [19]
Duncan et al.

[11] Patent Number: 5,765,243
[45] Date of Patent: Jun. 16, 1998

[54] PATIENT CARRIER

[75] Inventors: Matthew F. Duncan, Westminster; Gary R. Williams, Carlsbad; Steven A. Badolato, Laguna Beach, all of Calif.

[73] Assignee: Hartwell Medical Corporation, Carlsbad, Calif.

[21] Appl. No.: 795,957

[22] Filed: Feb. 28, 1997

[51] Int. Cl.[6] .................................................. A61G 1/003
[52] U.S. Cl. ................................. 5/625; 5/627; 128/870
[58] Field of Search ............................... 5/625, 626, 627, 5/628; 128/870

[56] References Cited

U.S. PATENT DOCUMENTS

| | | |
|---|---|---|
| D. 338,177 | 8/1993 | Kimball . |
| 524,824 | 8/1894 | Hiser ..................................... 5/627 |
| 1,965,644 | 7/1934 | Heffelfinger . |
| 2,417,378 | 3/1947 | Robinson . |
| 2,503,314 | 4/1950 | Atwood ................................. 5/627 |
| 2,514,128 | 7/1950 | Gomelski ............................. 5/625 |
| 3,125,766 | 3/1964 | Halperin . |
| 3,343,180 | 9/1967 | Lothschuetz . |
| 3,653,079 | 4/1972 | Bourgraf et al. . |
| 3,921,231 | 11/1975 | Bourgraf et al. . |
| 4,480,345 | 11/1984 | Dunn . |
| 4,854,305 | 8/1989 | Bremer . |
| 5,109,555 | 5/1992 | Fickler . |
| 5,263,213 | 11/1993 | Robertson et al. . |
| 5,473,784 | 12/1995 | Nixon et al. . |
| 5,560,059 | 10/1996 | McQueen . |
| 5,568,662 | 10/1996 | Gougelet . |

FOREIGN PATENT DOCUMENTS

46394 A  2/1982  European Pat. Off. ................ 5/625

*Primary Examiner*—Michael F. Trettel
*Attorney, Agent, or Firm*—J. F. McLellan

[57] ABSTRACT

A scoop type patient carrier having separable halves to facilitate placement of the halves beneath a patient, and configured to enable radiographic examination. The joint between the halves, and the points where the pivot and latch mechanisms are located, are laterally offset from the midline or longitudinal centerline of the assembled carrier. This arrangement results in the absence of any joint or line of separation in the upper and lower sections that are aligned with the carrier centerline, and which support the head and feet. This enables the carrier halves to be joined or separated without any accompanying movement of the head and feet of the patient.

18 Claims, 4 Drawing Sheets

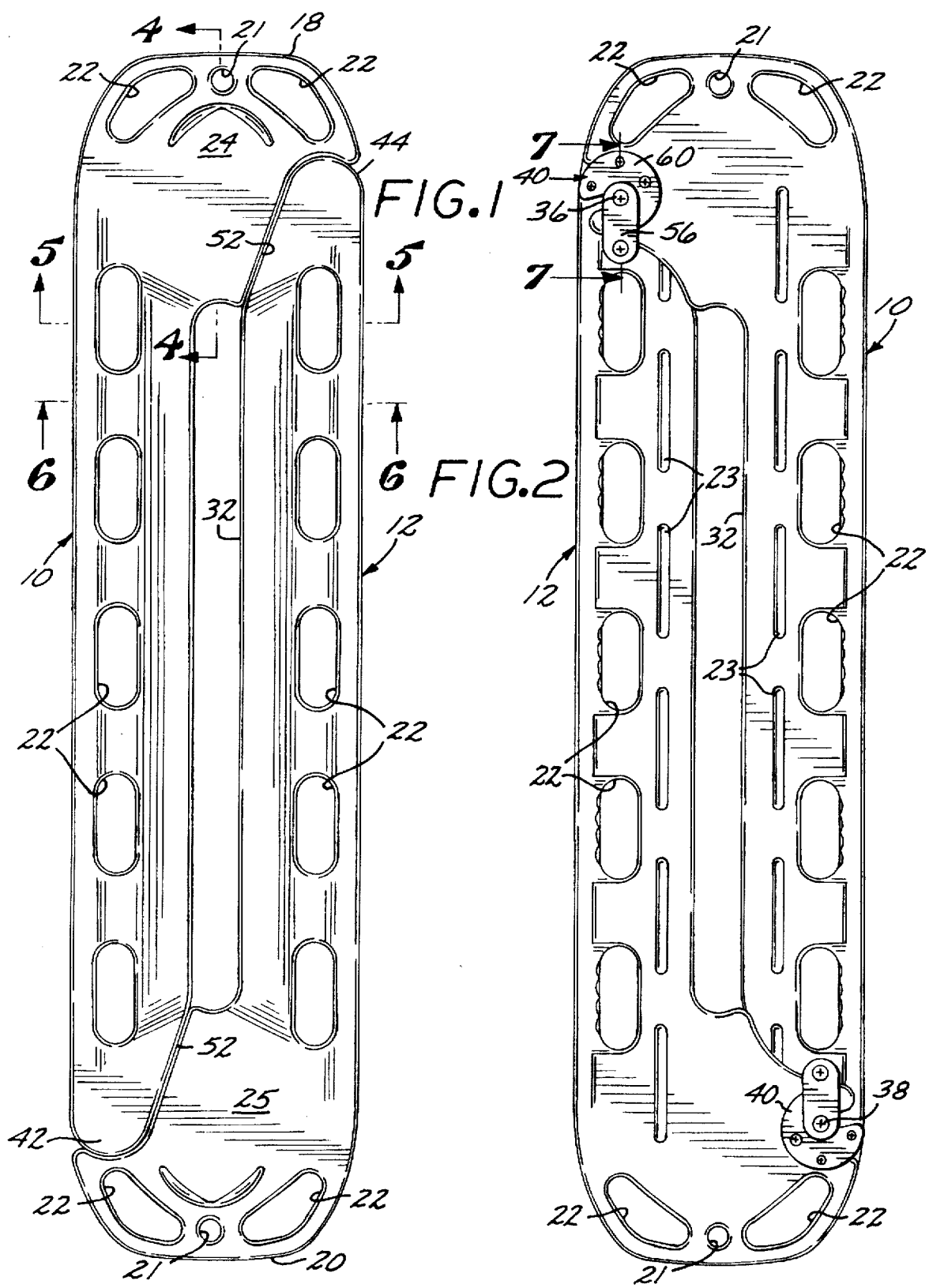

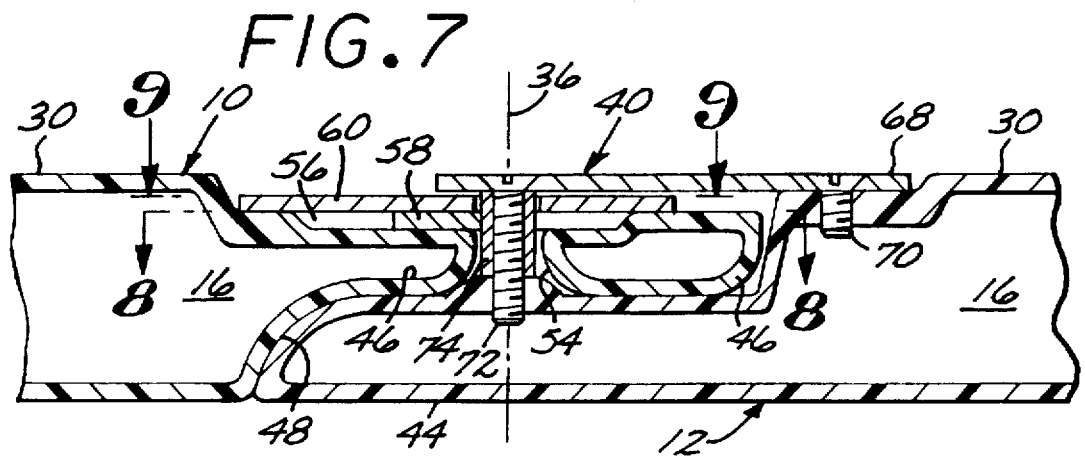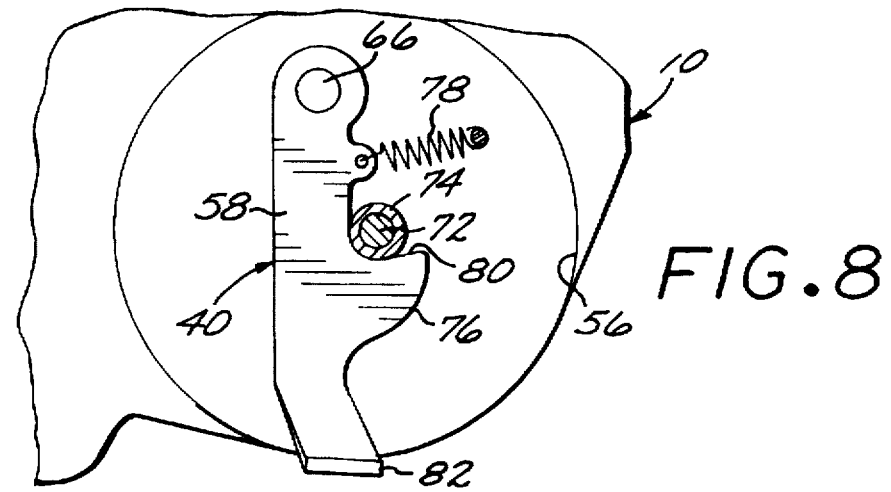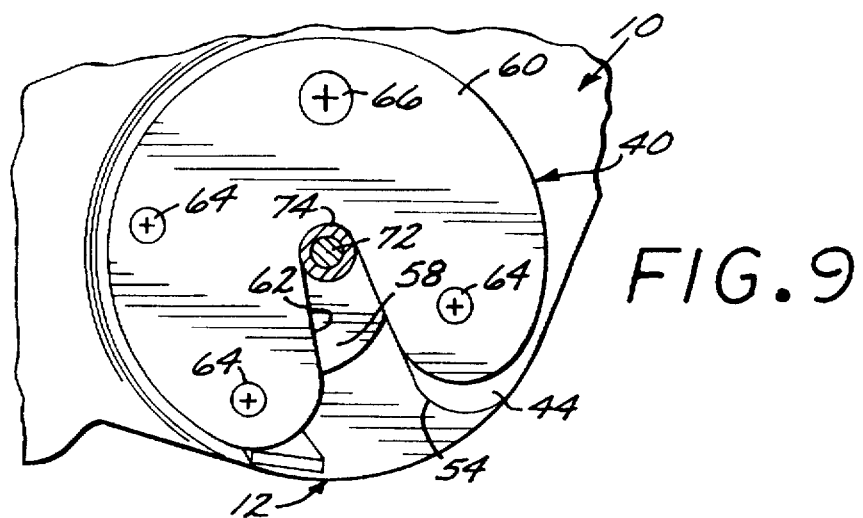

PATIENT CARRIER

BACKGROUND OF THE INVENTION

1. Field of the Invention

The present invention relates to a patient carrier which can be slipped beneath an injured or sick person with only slight movement of the person, and which also facilitates radiographic examination while the person is immobilized on the carrier.

2. Description of the Prior Art

Placement of an injured person upon a stretcher, body board or other carrier can result in secondary trauma to the head, neck or spinal column if great care is not exercised to minimize head and spinal movement. Similar care is required to avoid secondary injury when the person is transported to a care center or the like, or is radiographically examined while on the carrier.

Most accident victims or patients are prepared for transportation by placing them on a backboard or on a "scoop" stretcher. The hard surface of a backboard helps to constrain the patient against movement, but it is difficult to move the patient onto such a board without bending his body and consequently misaligning his spinal column. If the patient is lifted and lowered onto the carrier, the body sags in the middle.

Alternatively, if the patient is laterally placed onto the board, the patient has to be rolled or tipped up on one side, the board inserted beneath the patient, and the patient then rolled down onto the board and gently pulled laterally to center him on the carrier. Even when done carefully, this procedure involves considerable movement of the patient's head, neck and spine.

A scoop stretcher is an improvement over the backboard in that it does not require rolling the patient on his side. The scoop stretcher is made in two halves which have a concave or scoop shape at their inner margins. Some slight raising of one side of the patient is required to facilitate insertion of one scoop half under the patient, followed by similar slight raising on the other side to insert the other scoop half.

The inner margins of the scoop halves are spaced apart to avoid pinching the body when the halves are moved into position, and also to provide a central elongated space offering no obstruction to anterior-posterior radiographic examination of the spine. With the scoop stretcher there is much less movement required compared to a backboard.

Once in position, the opposite ends of the two scoop halves are locked together to define the "scoop" shape which gives the stretcher its name. The locked together stretcher can then be used to lift the patient onto a gurney and into a vehicle for transport to a hospital or other treatment center.

Most current "scoop" or "separable stretchers" are made of aluminum tube and aluminum sheet. This provides a degree of strength and rigidity, but an unwanted amount of deflection still occurs under load. Part of this is due to relative movement of the components at their points of connection, and part of it because of the use of small diameter tubing to save weight. In many instances the deflection is too great for the carrier to be acceptable as a spinal immobilization device.

The metal construction of such a carrier is also uncomfortably hot or cold during opposite weather extremes. Further, the surface irregularities and discontinuities existing at points of connection undesirably collect blood and other body fluids. These sites are difficult to clean and disinfect. The metal in the side panels of the structure also interfere with radiographic examinations.

The scoop type carriers just discussed are split down the middle when they are separated, and they close together along a midline when they are joined. There is therefore no fixed, centrally located unbroken or uninterrupted surface for the head. Thus, when the scoop halves are moved apart to separate them from the patient, the scoop halves underlying and supporting the head will split apart along their joint line and cause unwanted head movement.

The same thing is true when the halves are closed. Some movement of the head occurs when the halves move under the head.

Another disadvantage of the prior art centrally split scoop stretchers is that the hinge or connection points at the ends of the stretcher are centrally located. This means that the feet or head often have to be moved to gain access to these connection points for opening or closing of the carrier. As previously indicated, any movement of the patient's head, neck or spinal column is undesirable because of the possible aggravation of existing injuries.

The end shape or configuration of most scoop stretchers is not conducive to longitudinal or endwise receipt of a patient, as is desirable in extricating a patient from an automobile. Typically, the end structure is elevated above the main plane of the stretcher and forms an obstruction to such receipt.

In addition, the side structure of many scoop stretchers does not elevate the strap openings above the ground or other supporting surface.

This prevents the patient restraint straps from being fitted around the patient without first raising the stretcher to dispose the straps through the openings.

Examples of prior art one-piece or unitary backboard carriers are disclosed in U.S. Pats. Nos. Des. 338,177; 4,854,305; 5,473,784; 5,560,059; and 5,568,662.

Prior art embodiments of two-piece, separable scoop type patient carriers are found in U.S. Pats. Nos. 1,965,644; 2,417,378; 3,125,766; 3,343,180; 3,653,079; 3,921,231; 4,480,345; and 5,109,555.

SUMMARY OF THE INVENTION

According to the present invention, a patient carrier is provided which comprises a pair of separable halves, preferably substantially identical mirror images of each other to minimize inventory problems. The halves are configured so that they can be slipped or scoop fitted beneath an injured or otherwise incapacitated person.

An important feature of the carrier is the off center location of the carrier halves' mating line or connection joint. Also, in the case of a hinged pair of halves, the pivot points about which the halves hinge are also off center. The upper pivot point is preferably located adjacent an upper corner of one carrier half, and the lower pivot point is located off center and adjacent the diagonally opposite corner of the other carrier half. Thus, both the pivot points and the joint or line of juncture between the carrier halves are located in offset relation to the medial or longitudinal centerline of the joined halves.

By reason of this offset location of the joints between the carrier halves, as well as the offset location of the upper pivot point, a relatively flat and uninterrupted head support surface is defined adjacent the upper pivot point. The surface is slightly elevated in order to place the head in a neutral alignment position that generally corresponds to the normal anatomical position which a person's head and spinal column would assume when a person is standing straight with eyes forward.

Since the upper pivot point is located to one side of the head support surface, this surface is not interrupted by the joint or split line between the mating halves of the carrier, and therefore any relative movement occurring between the carrier halves is not accompanied by any movement of the head support surface. This eliminates any movement of the patient's head when the carrier halves are opened or closed.

In one embodiment of the invention each half of the carrier is hollow, being molded of relatively light weight, radiographically transparent plastic material. Except at the perimeter of the carrier halves, the upper and lower walls of the hollow interior in effect define spaced apart sections or skins, and the hollow interior is filled with a core material such as foam having good compression strength. The skins and core combination are characterized by a relatively high resistance to deflection to withstand heavy patient loading.

The carrier halves in their closed positions define a narrow central opening along the majority of the length of the longitudinal midline of the carrier to allow optimum patient exposure to anterior-posterior radiography, and also to avoid pinching of the patient upon closure and locking together of the halves.

The molding process facilitates the formation of usual hand hold openings about the periphery of the carrier, and the outer margins of the carrier are molded so that they are spaced slightly above the carrier center section to define hand and finger spaces for easy access to the handholds.

The handholds may include molded in pins or the like to which patient support or restraining straps can be quickly clipped.

The molding process also results in smoothly faired side extremities which are concave to allow for scoop-like insertion beneath a patient. The concave, inwardly directed side walls are engageable by the patient to limit the degree of transverse or lateral movement of the patient. In addition, the carrier halves taper at the ends to form relatively thin sections which facilitate end entry of a patient onto the board, either from a supine position, or from a seated position for extrication from an automobile, for example.

The plastic material of the carrier is electrically non-conductive and is selected for resistance to blood, body fluids, or petroleum based products such as diesel fuel. Its smoothly faired structure also makes it easy to clean and disinfect.

The halves of the carrier are characterized by latching mechanisms having complemental portions which automatically lock together when there is closure of the two halves, but which require a deliberate manual actuation to unlock the system for separation of the carrier halves. These mechanisms are also preferably located below the plane of the patient's spine in order not to adversely affect the clarity of radiographs.

Other aspects and advantages of the present invention will become apparent from the following more detailed description taken in conjunction with the accompanying drawings.

BRIEF DESCRIPTION OF THE DRAWINGS

FIG. 1 is a top plan view of a patient carrier illustrating a pair of carrier halves joined together, according to the present invention;

FIG. 2 is a bottom plan view of the patient carrier of FIG. 1;

FIG. 7 is an enlarged view, partly in section, taken along the line 7—7 of FIG. 2;

FIG. 8 is an enlarged view taken along the line 8—8 of FIG. 7; and

FIG. 9 is an enlarged view taken along the line 9—9 of FIG. 7.

DESCRIPTION OF THE PREFERRED EMBODIMENTS

Figure 3:
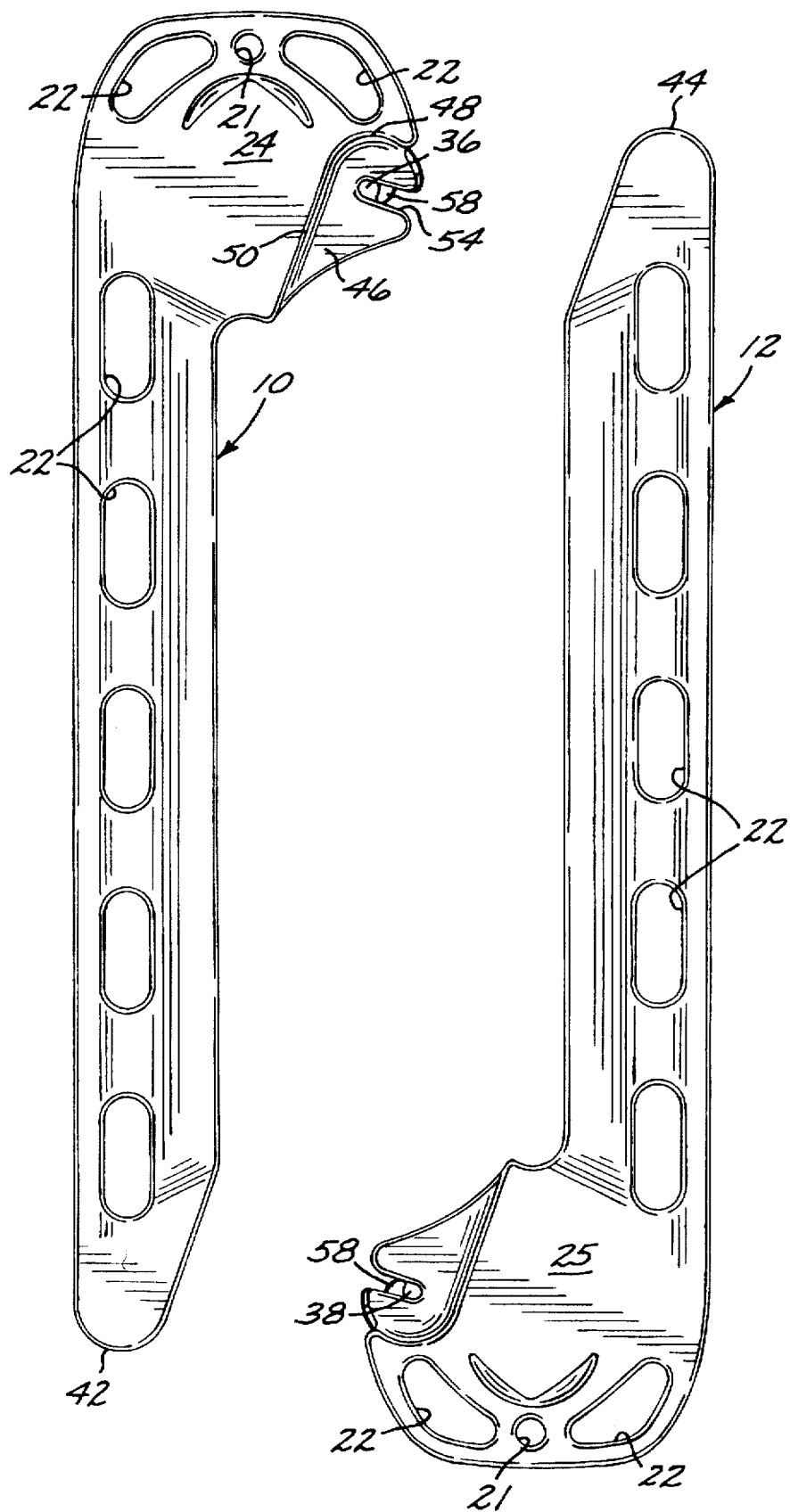
FIG. 3 is a top plan view of the patient carrier of FIG. 1 illustrating the carrier halves prior to their being joined together to form the patient carrier.

Referring now to the drawings, a patient stretcher or carrier is illustrated which comprises a pair of elongated carrier halves 10 and 12 which are preferably mirror images of each other, each being substantially identical in configuration. They are adapted to be joined to form a complete hermetically sealed carrier, as will be seen.

The halves 10 and 12 are preferably made using the well known rotational molding technique. In that process finely ground resin powders are heated in a rotating mold until melting or fusion occurs. The melted resin uniformly coats the inner surface of the mold and constitutes the wall 14 of the carrier half, as seen in FIG. 7.

When cooled, the carrier half is removed and the hollow skin or wall 14 of the carrier half is preferably filled by any suitable means with a core material 16 having satisfactory compression and bending strength. The filling opening is thereafter hermetically sealed. Alternatively, if desired, the foam material may be of a type which can be placed in the carrier structure prior to blow molding so that it will foam in place during the molding process. Either of these methods, or any other suitable method can be used to provide the desired sandwich core material within the hollow interior of the carrier.

If desired, the core material 16 could be eliminated, but the resistance of the carrier to deflection under the weight of a patient would be reduced. Consequently, the wall thicknesses of the carrier would have to be increased to compensate for elimination of the material 16.

The invention is not limited to any particular process of manufacture, nor to any particular materials for the wall 14 or the core material 16. Preferably the materials selected are waterproof, electrically non-conductive, wear resistant, and resistant to blood, bodily fluids and petroleum products such as diesel fuel. Furthermore, the materials should be radiographically transparent to facilitate both anterior-posterior as well as lateral radiographic examination of a patient on the carrier. In other respects, the materials selected should obviously be suited for the particular conditions that will be encountered.

The molding process produces a smooth exterior unbroken by any surface discontinuities that might collect blood or the like. This makes it easy to clean and disinfect the carrier.

Figure 4:
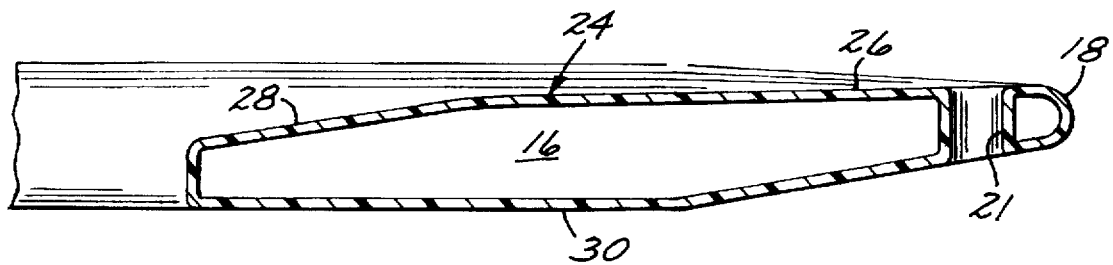
FIG. 4 is an enlarged view, partly in section, taken along the line 4—4 of FIG. 1.

The carrier halves include head and foot extremities 18 and 20, respectively, which taper at their end margins to a relatively thin edge, as best seen in FIG. 4. This facilitates slipping the thin edge under a patient for longitudinal or end loading of the patient onto the carrier from a narrow space, such as in an extrication procedure for removing a patient from the seat of an automobile. This minimizes movement of the patient. There are also no end structures on the carrier extremities which would obstruct or interfere with such loading, as compared with many prior art scoop carriers.

The carrier halves are also provided around the perimeter of the carrier with molded-in hand openings 22. In addition, the ends of the carrier halves include utility openings 21 for hanging the carrier on a peg or the like (not shown) for storage.

Figure 5:
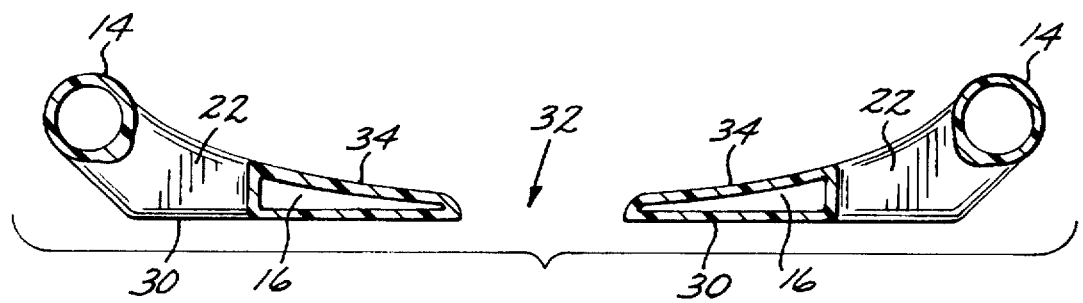
FIG. 5 is an enlarged view, partly in section, taken along the line 5—5 of FIG. 1.
Figure 6:
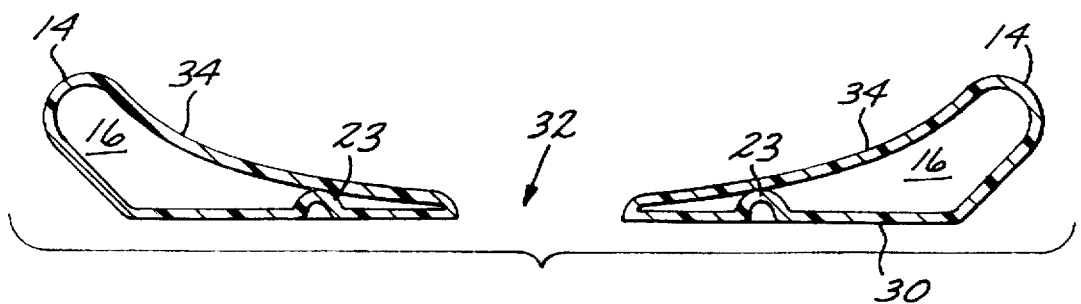
FIG. 6 is an enlarged view, partly in section, taken along the line 6—6 of FIG. 1.

The perimeter or edge periphery of each carrier half is smoothly faired into a round configuration, as best seen in FIGS. 5 and 6, to strengthen the carrier against bending and to form rugged hand supports. The periphery is slightly elevated above the lower surface of the carrier so that it will be located slightly above the ground or other supporting surface. The space below the round perimeter provides hand and finger space to gain easy access to the handholds.

The spacing of the round perimeter also enables patient encircling straps (not shown) to be passed through the hand openings, or clipped to integral rods (not shown) spanning a portion of the handholds. The carrier thus does not have to be lifted to position the straps through the hand openings.

The opposite ends or walls of the hand openings 22 provide resistance to deflection of the carrier halves under the load of a patient. In addition, the underside of the halves includes a series of longitudinally oriented indentations or grooves 23. These extend along opposite sides of the central opening 32, a separate one of the grooves 23 being located between each pair of hand openings 22. This strengthens the carrier halves against deflection. This is in addition to the rigidifying effect of the core material 16 in those instances where such core material is used.

With particular reference to FIGS. 1–3, each carrier half comprises the wider extremity 18 or 20, as the case may be, which is adapted to underlie the patient's head and feet, respectively.

The wider extremity 18, as best seen in FIG. 4, comprises a relatively flat head supporting surface 24. A similar foot supporting surface 25 is found in the extremity 20 of the other carrier half.

A forward portion 26 of the surface 24 is slightly inclined in a forward direction to smoothly merge with the rounded perimeter of the head end of the carrier. The forward portion 26 inclines rearwardly to smoothly merge with a rearward portion 28. The portion 28 inclines rearwardly somewhat more steeply, and terminates in a vertical wall that extends to join the undersurface 30 of the carrier half, as illustrated in FIG. 4.

This orientation of the portions 26 and 28 elevates the head supporting surface 24 above the carrier surfaces that support the patient's trunk. The patient's head will then be oriented in a neutral alignment position generally corresponding to the normal anatomical position of the spinal column when a person is standing straight with his eyes forward.

As best seen in FIGS. 1–3, 5 and 6, between the wider end extremities the carrier halves are characterized by narrow, longitudinally extending sides that are laterally spaced apart to define an elongated central space or opening 32. This opening extends along the longitudinal midline of the carrier and enables anterior-posterior radiography of the patient's spine. The existence of the opening also prevents a patient on the carrier halves from being pinched when the carrier halves are closed together, as will be seen.

Each of the carrier sides is smoothly faired laterally inwardly and downwardly from the outer rounded carrier perimeter. This forms a concave or scoop shaped trunk supporting surface 34. The inner margin or edge of the surface 34 is relatively thin for easy insertion beneath the trunk of a patient.

The concave surfaces 34 not only support the weight of the patient, but also tend to immobilize the patient against any lateral movement.

The connection or hinge points which pivotally connect the carrier halves together are located in laterally offset relation relative to the carrier midline. This asymmetrical relation, as seen in FIG. 2, locates the head end pivot axis 36 adjacent an outside corner of the extremity 18. The diagonally opposite foot end pivot axis 38 is correspondingly located adjacent an outside corner of the extremity 20. This arrangement places both axes 36 and 38 laterally outwardly of the respective head and foot supporting surfaces 24 and 25.

As a consequence, the surfaces 24 and 25 are uninterrupted by any split line or joint between the carrier halves. This is particularly important in the case of the head end pivot axis 36. Assuming a patient lying on the carrier is to be removed, separating movement of the carrier halves is not accompanied by any movement of the head, for example, because the joint line between the carrier halves is located to one side of the surface 25.

Likewise, when a patient is initially supported upon one carrier half, such as half 10, closure of the other half 12 to join with the half 10 does not cause any movement of the head of the patient. Thus, either upon pivotal joining or upon separating movement of the carrier halves, movement of the head is considerably less than is the case with scoop stretchers of the prior art. This is because in prior art stretchers the connection joints and pivot points lie along the midline of the carrier and therefore are located beneath the patients head and feet.

In the present carrier, the offset location of the pivot axes 36 and 38 is also advantageous in that the associated hinge and locking or latching mechanisms are also laterally offset, and access to them does not require movement of the patient's head and feet.

Each of the carrier halves includes a latching mechanism 40, as seen in FIGS. 2 and 7–9. The mechanism 40 includes complemental portions which automatically lock together when the two halves close, but which require deliberate manual actuation to unlock them.

Opposite its wide extremity 18, the carrier half 10 includes a narrow extremity 42. Likewise, opposite its wide extremity 20, the carrier half 12 includes a narrow extremity 44. As will be seen, the narrow extremity of each carrier half complementally fits with the wider extremity of the other carrier half.

In their upper surfaces, the wider extremities 18 and 20 each include a receptacle portion 46. These are identical in the carrier halves, and for brevity and simplicity only the portion 46 of the extremity 18 will be described, it being understood that the same description applies to the oppositely located portion 46 in the other extremity 20.

Using the orientation illustrated in FIG. 7, the underside of portion 46 is recessed to define a generally semicircular end wall 48 and a diagonally disposed side wall 50 to receive the narrow extremity 44 of the half 12.

The narrow extremity 44 includes a rounded end which closely and rotationally fits within the portion 46 adjacent the end wall 48 of the portion 46. The extremity 44 also includes a diagonal inner margin which closely fits against the side wall 50 of the carrier half 10. The mating line or juncture between the two carrier halves in this area forms a joint 52 which extends downwardly and inwardly to the upper terminus of the central longitudinal opening 32, as seen in FIG. 1. This laterally offsets the joints 52 from the carrier midline so that the joints 52 do not underlie a patient's head or feet.

As best seen in FIGS. 2 and 7–9, the receptacle portion 46 includes an entry throat or slot 54. Above the slot 54, as viewed in FIG. 7, the receptacle portion 46 is recessed to define a latch space 56 within which a latch 58 is pivotable, as will be seen.

A circular retainer plate 60 overlies the latch space 56 and includes a throat or entry slot 62 vertically aligned with the slot 54 in the receptacle portion 46. The plate 60 is attached to the portion 46 by three machine screws 64 and a larger machine screw 66. The larger screw 66 also supports the latch 58 for pivotal movement in the latch space 56.

The extremity 44 includes a recessed section which underlies the receptacle portion 46. Centrally of this recessed section is a raised area having a threaded opening.

A elongated relatively short strap 68 is fastened by a machine screw 70 at one end within a recessed area in the undersurface 30 of the extremity 44. The other end of the strap 68 is secured by a machine screw 72 which extends through a bushing 74 and into the threaded opening of the raised area in the extremity 44. This arrangement provides a bushing surface for engagement by the latch 58.

More particularly, when the extremity 44 is inserted into the receptacle portion 46, the bushing 74 enters both the slots 54 in the portion 46 and the slot 62 in the plate 60. The bushing 74 then engages an arcuate surface 76 of the latch 58 and rotates the latch about the screw 66 in a clockwise direction, as seen in FIG. 8, against the bias of a retaining tension spring 78. The opposite ends of the spring 78 are connected to the latch 58 and to the retainer plate 60.

The bushing 74 rides along the arcuate surface 76 until it reaches an inwardly extending cusp or detent 80. At this point the bushing 74 is moves onto the detent 80 and is captured there by the counterclockwise movement of the latch 58 in response to the spring 78. This automatically locks the extremities 18 and 44 of the carrier halves. A similar automatic locking action takes place to secure together the opposite extremities 20 and 42.

The carrier halves remain locked together until they are manually released. This is accomplished by pushing against a projecting release end 82 of the latch 58 to pivot the latch clockwise sufficiently for the bushing 74 to clear and move away from the detent 80. It is thus not possible for the carrier halves to separate without a deliberate manual action, which is a desirable safety feature.

In operation, an injured patient would be tipped up slightly on one side to permit insertion of the inner edge of one carrier half beneath the patient. Next, the inner edge of the other carrier is similarly inserted beneath the other side of the patient, and the extremities of the carrier halves are then locked together by the mechanisms just described. The unitary carrier can then be lifted for transporting the patient to a care center.

Removal of the patient at the care center is then a simple matter of manually unlocking the carrier halves to transfer the patient to a hospital bed or the like.

From the foregoing it will be apparent that the carrier enables a patient to be placed upon and removed from the carrier with minimum movement. In particular, the head of the patient is not moved by the carrier halves as a result of their junction or separation.

Various other modifications and changes may be made with regard to the foregoing detailed description without departing from the spirit of the invention.

What is claimed is:

1. A patient carrier comprising:

a pair of elongated carrier portions having respective head and foot supporting sections at their opposite extremities, the portions being movable together into a closed position in which the portions meet along joints between them that are located laterally outwardly of the supporting sections; and connecting means located adjacent and laterally outwardly of the supporting sections, respectively, the connecting means being operative to lock the carrier portions in the closed position, and further operative to unlock the carrier portions for separation along the joints for movement of the carrier portions out of the closed position, the head supporting section being unjointed and adapted to underlie the patient's head whereby the patient's head does not move upon separation of the carrier portions along the joints.

2. A patient carrier according to claim 1 wherein the carrier portions comprise substantially identical halves in which one carrier portion defines the head supporting section, and the other carrier portion defines the foot supporting section.

3. A patient carrier according to claim 1 wherein the portions define an elongated central patient receiving region and include inwardly directed concave surfaces adapted in the closed position to engage and constrain a patient located in the region against lateral movement.

4. A patient carrier according to claim 3 wherein the head support section is relatively flat and elevated above the central region thereby to maintain the head in a neutral alignment position relative to the spinal column of a patient located in the region.

5. A patient carrier according to claim 3 wherein the inwardly directed concave surfaces underlying the patient receiving region are spaced apart to define a central, longitudinally extending open area whereby anterior-posterior radiographic examination may be made of the head, neck and spinal column of a patient located in the region.

6. A patient carrier according to claim 1 wherein the connecting means comprises a post carried by one of the portions, wherein the other of the portions includes a slot adapted to receive the post in the closed position, and further including a latch in a blocking position across the slot and movable from the blocking position by the post upon movement of the post to the closed position.

7. A patient carrier according to claim 6 wherein the connecting means includes a bias means operative to urge the latch into the blocking position, the connecting means further including manually operative means for moving the latch out of the blocking position to release the post for movement out of the closed position.

8. A patient carrier according to claim 1 wherein the carrier portions comprise hollow shells made of radiographically pervious material filled with a substance resistant to compression forces.

9. A patient carrier according to claim 1 wherein the carrier portions are molded to define smooth exterior surfaces, and to include a plurality of openings in the periphery of the carrier defining handholds for lifting the carrier, the periphery adjacent the openings being raised above the lower surfaces of the carrier portions to facilitate insertion of a person's hands to grasp the handholds.

10. A patient carrier according to claim 1 wherein the carrier portions are molded to define smooth exterior surfaces, and the ends of the opposite extremities are tapered to facilitate slidable end entry of a patient onto the carrier.

11. A patient carrier comprising:

first and second elongated carrier halves which are substantially identical in configuration, the first carrier half having a head supporting section located at one extremity, the second carrier half having a foot supporting section located oppositely of the head supporting extremity, the halves being movable together into a closed position to form the carrier, the supporting sections in the closed position being located on opposite sides of the longitudinal axis of the carrier, the halves in the closed position meeting along joints located laterally outwardly of the supporting section; and connecting means located adjacent and laterally outwardly of the supporting sections, respectively, the connecting means being operative to lock the carrier halves in the closed position, and further operative to unlock the carrier halves for separation along the joints for movement of the carrier halves to an open position, the head supporting section being unjointed and adapted to underlie the patient's head whereby the patient's head does not move upon separation of the carrier portions along the joints.

12. A patient carrier comprising:

a pair of elongated carrier portions having respective head and foot supporting sections at their opposite extremities, the portions being movable together into a closed position in which the portions meet along joints between them that are located laterally outwardly of the supporting sections; and connecting means located adjacent and laterally outwardly of the supporting sections, respectively, the connecting means being operative to lock the carrier portions in the closed position, and further operative to unlock the carrier portions for separation along the joints for movement of the carrier portions out of the closed position, a post carried by one of the portions, wherein the other of the portions includes a slot adapted to receive the post in the closed position, and further including a latch in a blocking position across the slot and movable from the blocking position by the post upon movement of the post to the closed position.

13. A patient carrier comprising:

a pair of elongated carrier portions having respective head and foot supporting sections at their opposite extremities, the portions being movable together into a closed position in which the portions meet along joints between them that are located laterally outwardly of the supporting sections; and connecting means located adjacent and laterally outwardly of the supporting sections, respectively, the connecting means being operative to lock the carrier portions in the closed position, and further operative to unlock the carrier portions for separation along the joints for movement of the carrier portions out of the closed position, a post carried by one of the portions, wherein the other of the portions includes a slot adapted to receive the post in the closed position, and further including a latch in a blocking position across the slot and movable from the blocking position by the post upon movement of the post to the closed position, the connecting means including a bias means operative to urge the latch into the blocking position, the connecting means further including manually operatives means for moving the latch out of the blocking position to release the post for movement out of the closed position.

14. A patient carrier comprising:

a pair of elongated carrier portions having respective head and foot supporting sections at their opposite extremities, the portions being movable together into a closed position in which the portions meet along joints between them that are located laterally outwardly of the supporting sections; the portions defining an elongated central patient receiving region and including inwardly directed concave surfaces adapted in the closed positions to engage and constrain a patient located in the region against lateral movement, the head support section being relatively flat and elevated above the central region thereby to maintain the head in a neutral alignment position relative to the spinal column of a patient located in the region.

15. A patient carrier comprising:

a pair of elongated carrier portions having respective head and foot supporting sections at their opposite extremities, the portions being movable together into a closed position in which the portions meet along joints between them that are located laterally outwardly of the supporting sections; the portions defining an elongated central patient receiving region and including inwardly directed concave surfaces adapted in the closed positions to engage and constrain a patient located in the region against lateral movement, the inwardly directed concave surfaces underlying the patient receiving regions being spaced apart to define a central, longitudinally extending open area whereby anterior-posterior radiographic examination may be made of the head, neck and spinal column of a patient located in the region.

16. A patient carrier comprising:

elongated first and second carrier portions which each include longitudinally oppositely located head and foot extremities, one of the head extremities including a head support section;

the head extremity of the second carrier portion being adapted to pivotally interfit with the head extremity of the first carrier portion to define an open position in which the head extremities are interfitted and the foot extremities are spaced apart for receiving a patient upon the carrier;

the foot extremity of the second carrier portion being adapted to pivot into a closed position in which it is interfitted with the foot extremity of the first carrier portion;

first locking means having complemental components carried, respectively, by the head extremities of the carrier portions, the first locking means being operative to support the head extremities in the open position and to control the path of pivotal movement to the closed position of the second extremity of the second carrier portion; and second locking means having complemental components carried, respectively, by the foot extremities of the carrier portions, the second locking means being operative to support the foot extremities in the closed position for supporting a patient upon the carrier.

17. A patient carrier according to claim 16 wherein the line of separation between the head extremities that exists when the head extremities are in the open position lies outwardly of the head support section whereby relative movement of the head extremities between the open and closed positions does not result in movement of the patient's head.

18. A patient carrier according to claim 16 wherein the head support section forms a part of the head extremity of the first carrier portion.

* * * * *